US006287596B1

(12) United States Patent
Murakami et al.

(10) Patent No.: US 6,287,596 B1
(45) Date of Patent: Sep. 11, 2001

(54) QUICKLY DISINTEGRATABLE COMPRESSION-MOLDED MATERIALS AND PROCESS FOR PRODUCING THE SAME

(75) Inventors: Toshio Murakami; Hideaki Aritomi; Naoto Ueno, all of Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/147,501
(22) PCT Filed: Jul. 10, 1997
(86) PCT No.: PCT/JP97/02386
  § 371 Date: Jan. 11, 1999
  § 102(e) Date: Jan. 11, 1999
(87) PCT Pub. No.: WO98/02185
  PCT Pub. Date: Jan. 22, 1998

(30) Foreign Application Priority Data

Jul. 12, 1996 (JP) .................................................. 8-183278

(51) Int. Cl.$^7$ ............................................................ A61K 9/20
(52) U.S. Cl. .................... 424/464; 424/435; 424/441; 424/465; 514/770; 514/778; 514/781
(58) Field of Search .................................... 424/464, 465, 424/440, 441, 435, 439, 484, 488

(56) References Cited

U.S. PATENT DOCUMENTS 5,720,974 * 2/1998 Makino et al. ...................... 424/464
5,958,453 * 9/1999 Ohno et al. ........................... 424/465
5,973,212 * 10/1999 De Sadeleer et al. ................ 568/852

FOREIGN PATENT DOCUMENTS 0 553 777   8/1993   (EP) .

OTHER PUBLICATIONS

Derwent Publications, AN 1996–136212, JP 08 027033, Jan. 30, 1996.

Derwent Publications, AN 1996–500294, JP 08 256695, Oct. 8, 1996.

Derwent Publications, AN 1997–188301, JP 09 048726, Feb. 18, 1997.

* cited by examiner

*Primary Examiner*—James M. Spear
(74) *Attorney, Agent, or Firm*—Oblon, Spivak, McClelland, Maier & Neustadt, P.C.

(57) ABSTRACT

Quickly disintegratable compression-molded materials containing (a) fillers and (b) erythritol. These materials are highly disintegratable and soluble in the oral cavity or water and, therefore, can be easily taken. Also, they are highly hard and thus excellent in storage stability in the production and distribution stages. Owing to these characteristics, they can be appropriately blended with efficacious ingredients and used in the treatment or prevention of diseases in patients, in particular, the aged, infants or those having difficulty in swallowing.

65 Claims, No Drawings

QUICKLY DISINTEGRATABLE COMPRESSION-MOLDED MATERIALS AND PROCESS FOR PRODUCING THE SAME

This application is a 371 of PCT/JP97/02386 filed Jul. 10, 1997.

TECHNICAL FIELD

The present invention relates to a quickly disintegratable compression-molded material which has practically sufficient strength in handling of formulations in the field of pharmaceuticals and foods, and which disintegrates and dissolves quickly in the oral cavity or in water. The invention also relates to a process for producing such a material.

BACKGROUND ART

Solid peroral formulations known in the field of pharmaceuticals and foods include tablets, capsules, troches, chewable tablets, granules, and powders. However, not many formulations are designed for patient's ease in swallowing. There exists need for development of formulations which are easy to handle and easy to swallow for the aged, infants, and those having difficulty in swallowing. Tablets and capsules have drawbacks in that water is needed when they are taken. In addition, when the tablets are big or many tablets must be taken, patients have difficulty in swallowing or the tablets may become stuck within the pharynx or esophagus. These problems are very serious, especially to the aged, infants, and patients having difficulty in swallowing. Clogging of the throat sometimes suffocates such patients and medicines staying on the esophagus may cause inflammation. Troches are formulations which are gradually dissolved or disintegrated within the mouth for the application to the oral cavity or pharynx, and require no water. However, there is fear that they might stick within the pharynx or the esophagus when they are swallowed due to misuse. Chewable tablets need no water, being swallowed after chewing, but, they are not suitable for the aged or infants who have poor chewing force. Granules and powders require water for swallowing, and have drawbacks that they tend to stay in the oral cavity, choke the patient, and cause pain when they enter between false teeth.

In recent years, there is used a per tubam administration method in which medicines are given through a peroral or pernasal stomach tube catheter to a serious case having difficulty in swallowing. In practice, a prevailing method consists of injecting into the stomach tube catheter by use of a syringe a suspension prepared by adding crushed tablets or granules, or powdery medicines just as they are, to 20–30 ml of water. However, the procedures are complicated and the catheters are sometimes prone to clog since the inner diameter of the catheter is only 2–4 mm.

Against the foregoing background, there are known several formulations which are quickly disintegratable or soluble when put in the oral cavity or in water, and thus are suitable for the aged, infants, and those having difficulty in swallowing.

For example, Japanese Patent Publication (kokoku) No. 50445/1987 discloses a molded material having an open-matrix network structure obtained by filling molding pockets made of polyvinyl chloride sheet with an aqueous solution containing gelatin combined with a medicinal material, cooling and freezing the solution, and then freeze-drying the freezed solution. The publication describes that the open-matrix network structure has a density of 10–200 mg/ml, rapidly disintegrates within the oral cavity in 1–5 seconds, and is swallowed with sputum so as to prevent a patient who dislikes taking medicine from spitting it out.

In countries outside Japan, an intraoral soluble formulation known as Zydis (brand name) is commercialized by R. P. Scherer (England). The composition of the formulation is not known, but the formulation is manufactured by use of a freeze-drying process. The formulation manufactured by freeze-drying has the advantage of rapid disintegration, but it is fragile and brittle to such an extent that the hardness cannot be measured. Moreover, productivity of the formulation on an industrial scale is inferior because freeze-drying manufacturing equipment and long fabrication times are required.

International Patent Publication No. WO 93/12769 discloses an intraoral disintegratable formulation obtained by suspending a medicinal substance, lactose, and mannitol in an agar aqueous solution, solidifying the solution into a jelly state by charging the solution into molding pockets made of PTP (Press Through Package) sheet (made of polypropylene), drying the jelly under reduced pressure, and then sealing PTP-packaged products with aluminum foil. The obtained molded material has a density of 400–1000 mg/ml and is disintegrated in the oral cavity in 5–20 seconds. The publication describes that the molded material has a hardness of about 2 kg, and removal of the molded material from the PTP package does not result in cracking, crushing, or chipping. However, since the molded material has low strength as compared with conventional tablets, the material cannot be packaged in other than a PTP package, such as a bottle package. Also, productivity of the material on an industrial scale is inferior because of a long time needed for fabrication.

Several interoral disintegratable formulations which can be produced by a tableting method have been reported.

Japanese Patent Application Laid-Open (kokai) No. 271054/1993 discloses an intraoral disintegratable formulation which is obtained by tableting a mixture containing a pharmaceutically active ingredient, a carbohydrate, and a barely sufficient amount of water to moisten the surface of particles of the carbohydrate.

International Patent Publication No. WO 93/15724 discloses a rapid soluble tablet having two characteristics:

(1) the main component of the tablet is a medicinal additive having a high dissolution rate in water; and
(2) during a process where tablets containing medicinal material are produced by use of a wet granulation method, a kneaded mixture of medicinal material and medicinal additives having a high dissolution rate in water is compression molded and then dried.

Japanese Patent Application Laid-Open (kokai) No. 218028/1994 discloses:

(1) a molding method for producing tablets through a wet process, characterized by filling a mold with wet kneaded material and molding the material by use of compression molding; and
(2) a molding method for producing tablets through a wet process, in which before wet tablets are compression-molded, powder is applied on the compressed surface or the compression-punched surface of wet tablets in order to prevent wet tablets from sticking when being compressed.

Japanese Patent Application Laid-Open (kokai) No. 19589/1996 discloses a method of manufacturing tablets by charging wet powder into holes for molding tablets, and forming the powder into the tablet shape by use of a mold for molding after application of a stick-prevention film on at least one surface of the above-mentioned wet powder within the hole.

Since these methods are wet tableting methods, they use a wetting agent during molding, and molding is performed under low pressure. Therefore, they provide porous tablets having proper voids after drying and which are soft and easily disintegrated.

However, because these methods involve charging and compressing wet powder having poor fluidity, they have the disadvantage that the amount of charged material varies and sticking often occurs. Moreover, they require special drying equipment for drying soft molded material while retaining shape, and productivity on an industrial scale is inferior.

To solve this problem, an interoral disintegratable formulation produced by a dry tableting method of superior productivity has been reported.

Japanese Patent Application Laid-Open (kokai) No. 310558/1993 discloses that a highly disintegratable solid formulation composition that enables reduction of the amount of other additives having high molding characteristics; for example, cellulose-based compounds, acrylic compounds, or gelatin and the like, is obtained by mixing mannitol or lactose, which has poor bonding and molding characteristics, and sorbitol powder or granule having a bulk density of 60 g/100 ml.

International Patent Publication No. WO 95/20380 discloses an intraoral disintegratable compression molded product having rapid disintegrability and solubility in the oral cavity which is obtained by incorporation of saccharides having low molding characteristics and saccharides having high molding characteristics. This publication discloses that the compression molded product has a hardness of 3–6 kg for a tablet of a diameter of 10 mm$\phi$ and a dissolution time of 15–25 seconds in the oral cavity. However, punching pressure is 50–400 kg/stroke (64–509 kg/cm$^2$) and is rather low as compared with common punching pressure about 1000 kg/cm$^2$. This suggests that the resultant molded product is brittle as compared with conventional tablets and has a very low falling impact strength.

A tablet obtained by molding under low punching pressure has a high disintegrability and dissolution rate but has a low hardness. A tablet obtained by molding under high punching pressure has a high hardness but has a low disintegrability and dissolution rate.

Conventional tablets have a high hardness that does not permit breakage during production and distribution; however, since they are designed to release the pharmaceutically active ingredient through disintegration and dissolution of the perorally administered tablets in the digestive tract, they are given no consideration of prompt disintegration and dissolution in the oral cavity. Consequently, the tablets exhibit insufficient disintegrability and solubility in the oral cavity. No known tablet exhibits rapid disintegration and dissolution in the oral cavity and, at the same time, high hardness.

Therefore, there remains need for tablets which exhibit rapid disintegration and dissolution when placed in the oral cavity or water and which do not collapse throughout the processes of manufacture and distribution.

An object of the present invention is to provide a quickly disintegratable compression-molded material which exhibits rapid disintegration and dissolution when placed in the oral cavity or water and which is endowed with high strength that does not permit collapse thereof throughout the processes of manufacture and distribution.

Another object of the present invention is to provide a method of excellent industrial productivity for the manufacture of a quickly disintegratable compression-molded material having excellent characteristics as described above, without need for intricate steps or complicated facilities, through use of a dry method which is employed in customary tableting methods.

DISCLOSURE OF THE INVENTION

The present inventors have conducted careful studies in an attempt to solve the above-described problems, and have found that when a mixture of erythritol and an ingredient selected from among organic and inorganic excipients is tableted, quite surprisingly there can be obtained a quickly disintegratable compression-molded material which exhibits rapid disintegration and dissolution when placed in the oral cavity or water and which is endowed with high strength that does not permit collapse thereof throughout the processes of manufacture process, thus leading to completion of the invention.

Accordingly, the present invention provides a quickly disintegratable compression-molded material characterized by comprising (a) an excipient, and (b) erythritol.

MODES FOR CARRYING OUT THE INVENTION

As used herein, the expression "a quickly disintegratable compression-molded material" refers to a compression-molded material having practically sufficient strength throughout the processes of manufacture and distribution of the formulation.

Examples of excipients which are used in the present invention include inorganic excipients, and organic excipients selected from among starches, celluloses, and sugar alcohols.

Examples of starches include corn starch, potato starch, wheat starch, rice starch, partly pregelatinized starch, pregelatinized starch, hydroxypropyl starch, and sodium carboxymethyl starch. Of these, cornstarch, partly pregelatinized starch, and pregelatinized starch are preferred. No limitation is imposed on the grain diameter of the starches which are usable in the present invention. However, the grain diameter of the starches is preferably not more than 500 μm, from the viewpoint that larger granules tend to cause rough sensation to the oral cavity.

Examples of celluloses include microcrystalline cellulose, powdered cellulose, low substituted hydroxypropyl cellulose, carmellose, carmellose-Ca, and cross carmellose-Na. Of these, microcrystalline cellulose, powdered cellulose, low substituted hydroxypropyl cellulose, and carmellose are preferred. There is no limitation on the grain diameter of the cellulose used in the present invention. Preferably, the grain diameter of cellulose is 500 μm or less, from the viewpoint that larger granules tend to cause rough sensation to the oral cavity.

Examples of sugar alcohols include sugar alcohols other than erythritol; for example, D-mannitol, D-sorbitol, xylitol, maltitol, anhydrous maltose, hydrous maltose, anhydrous lactitol, hydrous lactitol, and reducing malt sugar syrup. Of these, D-mannitol, xylitol, and multitol are preferred. No particular limitation is imposed on the grain diameter of the sugar alcohol used in the present invention. Preferably, the grain diameter is 500 μm or less, from the viewpoint that larger granules tend to cause rough sensation to the oral cavity.

Examples of the inorganic excipients which may be used in the present invention include synthetic hydrotalcite, precipitated calcium carbonate, anhydrous dibasic calcium phosphate, hydrated silicon dioxide, light anhydrous silicic acid, calcium silicate, magnesium alminosilicate, magnesium oxide, and magnesium hydroxide. Of these, synthetic hydrotalcite, precipitated calcium carbonate, and anhydrous dibasic calcium phosphate are preferred. No particular limitation is imposed on the grain diameter of the excipients used in the present invention. Preferably, the grain diameter is 500 μm or less, from the viewpoint that larger granules tend to cause rough sensation to the oral cavity.

These excipients may be used singly or in combination.

Erythritol in the present invention is a sweetener obtained through fermentation of glucose and is a tetrahydric sugar alcohol represented by the following formula.

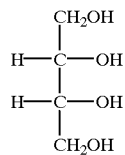

Erythritol is a white crystalline powder having a melting point of 119° C., and is freely soluble in water. The heat of dissolution of erythritol is −42.9 cal/g. It is a sweetener which provides a cool sensation, exhibits no moisture-absorbing properties, and has a sweetness degree which is equivalent to 70–80% that of sugar. No particular limitation is imposed on the grain diameter of the erythritol used in the present invention. However, in view that larger granules tend to cause rough sensation to the oral cavity, erythritol having a grain diameter of 500 μm or less is preferred.

The total amount of excipient (a) and erythritol (b) preferably falls within the range of 30–99% by weight, more preferably 50–99% by weight, most preferably 70–99% by weight, of the total weight of the quickly disintegratable compression-molded material. Amounts less than 30% by weight lead to insignificant contribution of these ingredients, resulting in poor disintegration and dissolution.

The ratio of excipient (a) to erythritol (b) is preferably 5–100% by weight, more preferably 10–70% by weight, most preferably 20–50% by weight. If no excipient (a) is incorporated, tableting troubles (capping phenomenon; in which the top portion of the tablet cracks laterally to assume the appearance of a hat) tends to occur, which can be prevented by incorporation of excipient (a) to erythritol (b). On the other hand, when the ratio of excipient (a) to erythritol (b) is in excess of 100% by weight, contribution of erythritol is insignificant, resulting in a prolonged time in terms of disintegration and dissolution. Particularly in the case of celluloses, they are preferably incorporated in an amount of 5–70% by weight, more preferably 5–50% by weight, with respect to the amount of erythritol.

No particular limitation is imposed on the pharmaceutically active ingredients which may be used in the present invention, and they may be added in accordance with intended uses in the form of powder, crystals, oil, solutions, or in any other forms. Instead of the active ingredients, other optional ingredients may be added. Examples of such optional ingredients are described below.

Examples of vitamins include vitamin A, vitamin D, vitamin E (such as d-α-tocopherol acetate), vitamin $B_1$ (such as thiamin hydrochloride), vitamin $B_2$ (such as riboflavin), vitamin $B_6$ (such as pyridoxine hydrochloride), vitamin C (such as ascorbic acid and sodium ascorbate), vitamin $B_{12}$ (such as hydroxocobalamin acetate), nicotinamide, calcium pantothenate, and pantethine.

Examples of antipyretic analgesic antiinflammatory agents include aspirin, acetaminophen, ethenzamide, ibuprofen, ketoprofen, indomethacin, and aminopyrine.

Examples of antihistaminic agents include alimemazine tartrate, chlorpheniramine maleate, diphenhydramine hydrochloride, clemastine fumarate, carbinoxamine maleate, dimenhydrinate, and meclizine hydrochloride.

Examples of antitussives include codeine phosphate, dihydrocodeine phosphate, dextromethorphan hydrobromide, noscapine, and noscapine hydrochloride.

Examples of bactericides include cetylpyridinium chloride, dequalinium chloride, chlorhexidine chloride, iodine, and potassium iodide.

Examples of antacids include magnesium alminosilicate, magnesium alminometasillicate, synthetic hydrotalcite, synthetic aluminum silicate, magnesium oxide, sodium bicarbonate, magnesium carbonate, precipitated calcium carbonate, anhydrous dibasic calcium phosphate, and scopolia extract.

Examples of crude drugs include aloe, fennel, phellodendron bark, captis rhizome, glycyrrhiza, cinnamon bark, amomum seed, swertia herb, rhubarb, ginseng, mallotus bark, Corydalis Tuber, and ephedra harb.

Examples of gastric mucosal protective agents include cetraxate hydrochloride, sodium azulene sulfonate, aldioxa, L-glutamine, sodium copper chlorophyllin, and methylmethionine sulfonium chloride.

Examples of analgetic antispasmodic agents include N-methylscopolamine methylsulfate, scopolamine hydrobromide, atropine methyl bromide, methylscopolamine bromide, belladonna extract, scopolia extract, ethyl aminobenzoate, scopolamine butyl bromide, and timepidium bromide.

Examples of anticonstipation agents include aloe, rhubarb, bisacodyl, and sodium picosulfate.

Examples of psychotropic agents include timiperone, oxypertine, diazepam, nitrazepam, flunitrazepam, lorazepam, haloperidol, and bromperidol.

Examples of H2 receptor antagonists include cimetidine, famotidine, ranitidine hydrochloride, nizatidine, and roxatidine acetate hydrochloride.

Examples of antiulcer agents include cetraxate hydrochloride, teprenone, sulpiride, sucralfate, plaunotol, and gefarnate.

Examples of antibiotics include tetracycline, oxytetracycline, metacycline, doxycycline, minocycline, chloramphenicols, and erythromycins.

Examples of antihypertensives include budralazine and hydralazine hydrochloride.

Examples of antiarrhythmic agents include pilsicainide hydrochloride and procainamide hydrochloride.

Examples of central nervous system stimulants include caffeine, anhydrous caffeine, and caffeine and sodium benzoate.

The pharmaceutically active ingredients in the present invention may be used singly or in combination. Examples of preferable effective ingredients include antipsychotic agents, antihistaminic agents, H2 receptor antagonists, antiulcer agents, vitamins, gastrointestinal agents, antitussive and expectorant drugs, anticonstipation agents, antivertigos (anti-motion-sickness drugs), and central nervous system stimulants. Further, not only to pharmaceuticals for humans, these ingredients may be applied to veterinary pharmaceuticals, agricultural chemicals, and diagnostic drugs. The present invention may also be applied to many uses which may obtain benefits from the features of the present invention; for example, health foods, nutritional supplement foods, ozostomia removers, plaque stain, bath-additive agents, and detergents.

The amounts of the pharmaceutically active ingredients vary depending on their properties. The amounts are 1–70% by weight, preferably 1–50% by weight, more preferably 1–30% by weight, of the solid contents.

The present invention may contain a variety of additives which are usually used for production of tablets, so long as the effects of the invention are not impeded.

Examples of such additives include lubricants, disintegrants, diluents, binding agents, coloring agents, flavoring agents, sweeteners, corrigent, effervescent agents, and surfactants.

Examples of lubricants include magnesium stearate, calcium stearate, stearic acid, talc, sucrose fatty acid esters, polyethylene glycol, and hydrogenated oils.

Examples of disintegrants include alginic acid, calcium alginate, powdered traganth, crospovidone, powdered agar, and bentonite.

Examples of diluents include lactose, sucrose, glucose, fructose, light anhydrous silicic acid, calcium silicate, and calcium lactate.

Examples of binding agents include acacia, sodium alginate, carboxyvinyl polymers, gelatin, dextrin, pectin, sodium polyacrylate, pullulan, methylcellulose, hydroxypropylcellulose, hydroxypropylmethylcellulose, polyvinyl alcohol, polyvinyl pyrrolidone, and macrogol.

Examples of coloring agents include food coloring agents such as food yellow No.5, food red No.2, and food blue No.2, food lakes, yellow ferric oxide, red ferric oxide, titanium oxide, β-carotene, and riboflavin.

Examples of flavoring agents include oranges, lemons, peppermint, and menthol. Examples of the sweeteners include saccharin sodium, aspartame, dipotassium glycyrrhizinate, stevia, and thaumatin.

Examples of taste improvers include sodium chloride, magnesium chloride, disodium inosinate, sodium L-glutamate, and honey.

Examples of the effervescent agents include combinations of an acid such as citric acid, tartaric acid, or malic acid and a base such as sodium bicarbonate or sodium carbonate.

Examples of the surfacants include polyoxyl 40 stearate, sorbitan esters of fatty acid, polyoxyethylene hydrogenated castor oil, polysorbate, glyceryl monostearate, and sodium monododecyl sulfate.

The above-listed additives may be added singly or in combination at any stage of the process for producing a rapidly disintegratable compression-molded material. For example, these additives may be added as desired in suitable amounts during mixing of the pharmaceutically active ingredient, excipient (a), and erythritol (b), or when water is added, or during granulation; or before or after any one of these processes.

The rapidly disintegratable compression-molded material of the present invention is manufactured, for example, through compression-molding of a substantially dry composition which contains an excipient (a) and erythritol (b). More specifically, the rapidly disintegratable compression-molded material of the present invention is manufactured by directly, or after granulation, bringing to substantial dryness the excipient (a), erythritol (b), and if needed, a pharmaceutically active ingredient and the aforementioned additives, followed by tableting. Details of the process are as follows.

Method 1
Excipient (a), erythritol (b), and as necessary, a pharmaceutically active ingredient and the aforementioned additives are mixed and compression-molded (direct compression method).

Method 2
Excipient (a), erythritol (b), and as necessary, pharmaceutically active ingredients and the aforementioned additives are mixed, formed into flakes, compression-molded to form tablets or slug tablets (large tablets) by compression, then crushed into granules, and if desired, combined with the aforementioned additives, dried to a substantially dry state, followed by compression-molding (dry granulation-tableting method).

Method 3
Excipient (a), erythritol (b), and as necessary, pharmaceutically active ingredients and the aforementioned additives are mixed. The mixture is granulated by adding water or an aqueous solution or suspension of starch and/or sugaralcohol, followed by granulation. The granules are substantially dried. Thereafter, the aforementioned additives are added as desired. The resultant mixture is substantially dried and compression-molded (wet granulation-compression method).

Method 4
The pharmaceutically active ingredients are divided into groups A and B, and through the wet granulation-tableting method referred to as Method 3, their respective granules are prepared. If necessary, the aforementioned additives are further added. The resultant mixture is brought to substantial dryness, followed by compression-molding (multi-type-granule-compression method).

The quickly disintegratable compression-molded material of the present invention is produced by use of an apparatus which is generally used in the manufacture of formulations. Specifically, mixing is performed by use of a twin-shell blender, a fluidized bed granulator, an agitated glanulating machine, a nauta mixer, or a cross rotary mixer.

For obtaining flakes compression molded product through dry granulation, a dry granulator is used, and for compression-molding of slug tablet, a rotary tabelting machine is used.

Wet granulation is performed by use of a fluidized bed granulator, a rotating fluid bed granulation and coating machine, an agitated granulating machine, a cylindrical extruting granulator, or a wet-type extruting granulator.

Compression-molding is performed by use of an apparatus which is generally used for molding tablets. For example, there is used a single-punch tablet machine, rotary tableting machine, or a multilayer rotary tablet machine.

The molding pressure during tableting can be arbitrarily determined based on the hardness of the molded material, and disintegration and dissolution properties of the molded material when put into the oral cavity or water. A characteristic feature of the present invention is that the disintegration and dissolution properties of the molded material when put into the oral cavity or water are not significantly marred even when the material has undergone an increased molding pressure. Thus, the molding pressure may be as high as that applied to common tablets; i.e., 400–2000 kg/cm$^2$, preferably 600–1800 Kg/cm$^2$, more preferably 800–1600 kg/cm$^2$. The density of the molded material is 800–1600 mg/cm$^3$, preferably 1000–1400 mg/cm$^3$. The hardness is regulated to not less than 2 kg, preferably 2–15 kg, more preferably 3–10 kg, for the case in which the diameter or the major length of the quickly disintegratable compression-molded material is 10 mm.

The thus-obtained quickly disintegratable compression-molded material is endowed with excellent disintegration and dissolution properties when put in the oral cavity or water, has improved hardness, and exhibits excellent falling impact strength.

The disintegration and dissolution properties of the quickly disintegratable compression-molded product of the present invention differ depending on the size of the product. Preferably, the disintegration time as measured according to the Japanese Pharmacopoeia (see the disintegration test method (without use of an auxiliary disk) described in the Japanese Pharmacopoeia 12th Revision, under the heading "Tablets") is within 60 seconds for the case in which the diameter or the major length of the quickly disintegratable compression-molded material is less than 8 mm; within 90 seconds for the case of the size being not less than 8 mm and less than 10 mm; within 120 seconds for the case of the size being not less than between 10 mm and less than 15 mm; within 180 seconds for the case of the size being not less than between 15 mm and less than 20 mm; and within 240 seconds for the case of the size being not less than 20 mm. Also, the disintegration and dissolution properties in the oral cavity as measured in terms of time required for disintegration or dissolution is within 40 seconds in the case in which the diameter or the major length of the quickly disintegratable compression-molded material is less than 8 mm; within 60 seconds for the case of the size being not less than 8 mm and less than 10 mm; within 90 seconds for the case of the size being not less than between 10 mm and less than 15 mm; within 120 seconds for the case of the size being not less than between 15 mm and less than 20 mm; and within 180 seconds for the case of the size being not less than 20 mm, all determined when the material is put in the oral cavity. Specifically, preferable disintegration time is generally 5–120 seconds, preferably 5–60 seconds, more preferably 5–30 seconds, in the case in which the diameter or the major length of the quickly disintegratable compression-molded material is less than 10 mm, and the time required for disintegration and dissolution in the oral cavity (i.e., the time required for a tablet to be dissolved completely in the oral cavity of a healthy adult man, without use of water but only use of saliva) is typically 5–90 seconds, preferably 5–60 seconds, most preferably 5–30 seconds.

When placed in the oral cavity, the rapidly disintegratable compression-molded material of the present invention disintegrates or dissolves in the presence of saliva. Application of pressure in the oral cavity, namely pressure applied by the upper jaw and the tongue, or through friction produced against the tongue, namely "licking" movement, etc., causes the tablet to be disintegrated or dissolved in a shorter time. When the tablet is taken by a subject having a dry mouth, or by a subject who secretes less saliva, cold water or warm water may be used for disintegration and dissolution of the tablet in the oral cavity. Alternatively, the tablet of the present invention may be taken exactly in the same manner together with water, as in the case of conventional tablets.

The rapidly disintegratable compression-molded material of the present invention does not disintegrate or dissolve instantaneously (e.g., within 1 sec), allowing the user to enjoy the intraoral organolestic sensation or spit the tablet if desired.

The hardness (as measured by use of a tablet hardness tester) of the rapidly disintegratable compression-molded material of the present invention is typically not less than 2 kg, preferably 2–15 kg, more preferably 3–10 kg, in the case in which the diameter or the major length of the quickly disintegratable compression-molded material is 10 mm. The falling impact strength (which is a breakage ratio obtained when a tablet is allowed to fall from the height of 50 cm onto a stainless steel plate, and defined by: {(broken tablets)/(tested tablets)}×100(%)) is typically about 0–50%, preferably 0–20%, more preferably 0%.

Thus, the rapidly disintegratable compression-molded material of the present invention exhibits enhanced hardness that does not permit breakage of the process of manufacture and distribution. Also, the tablet satisfactorily endures through the operation of removal thereof from a PTP package. Moreover, the tablet has a harness that allows packaging in bottles (i.e., packaging using a container made of, for example, glass or plastics). When tablets are taken out of aluminum sheet of a PTP package, in the case in which tablets having a diameter of 8 mm are concerned, it is preferred that they exhibit a hardness of 1 kg or more, and in the case in which tablets having a diameter of 10 mm are concerned, it is preferred that they exhibit a hardness of 2 kg or more, although the size and shape of the tablets may shift the range. In the case of packaging in a bottle, preferably, the tablets, if they are 10 mm in diameter, have a hardness of 3 kg or more so as to endure impact which may be applied during the process of ditribution.

The quickly disintegratable compression-molded material of the present invention contains a sweetener erythritol as a base material. Erythritol provides cool sensation and sweetness to the tablet. Also, since erythritol is a sugaralcohol, Mailard reaction (browning of an amino acid and a saccharide, also called an amino-carbonyl reaction) does not occur. This is advantageous in that the presence of a pharmaceutical ingredient having an amino group prevents the browning phenomenon, which means improved stability over time.

The quickly disintegratable compression-molded material of the present invention is used as a formulation that can be easily taken by the aged or infants, or as a formulation which is safely taken by normal adults, for the treatment or prevention of a variety of diseases, in the same manner as in the case of conventional formulations. Also, the material exhibits excellent long-term storageability and stability.

The shape of the quickly disintegratable compression-molded material of the present invention is not particularly limited. Examples of the shape of tablets include triangle, square, round, animal-shape, irregular shape (Caplet-type), ring (donut shape), multi-layer tablet, dry coated tablet, etc. In addition, letters or characters may be marked or applied for discernment. Tablets may be coated by a coating method which is customarily employed for the manufacture of coated formulations.

EXAMPLES

The present invention will next be described in detail by way of example, which should not be construed as limiting the invention thereto.

Test Method

In order to more fully describe the effects of the present invention, the tablets obtained in Reference Examples and Examples were tested for the following formulation characteristics.

(1) Hardness test

A tablet hardness tester (manufactured by Freund Sangyo K. K.; Schleuniger tablet hardness tester) was used to measure the hardness in the direction of diameter. The test was conducted for 5 tablets, and averaged data are shown.

(2) Intraoral disintegration and dissolution test

Three healthy adult men (age: 25, 30, and 30) participated in the test. The time required for the tablet to be completely disintegrated or dissolved with their intraoral saliva (without water) was measured. The averaged results from the three persons are shown.

(3) Disintegration test

According to the disintegration test described in the Japanese Pharmacopoeia, the 12th Revision, under the heading "Tablets," data were collected without use of an auxiliary disk (a disintegration tester made by Toyama Sangyo K. K.). The test was conducted on six tablets and averaged results are shown.

(4) Falling impact test

A tablet was allowed to fall from the height of 50 cm onto a stainless steel plate, and the breakage ratio was determined. Ten tablets were tested for each case and the obtained breakage ratios are shown.

(5) Punching pressure

The punching pressure was measured. Punching pressures per stroke (kg/stroke) as well as corresponding values converted to the punching pressure per unit area (kg/cm$^2$) are shown; the results are shown in average pressures.

(6) Density of tablets

Ten tablets were measured for their weight and thickness. The averaged measurements were used to calculate the density of the tablet. Tablet density=(Weight of the tablet)/(Volume of the tablet).

Reference Example 1

For referential purposes, erythritol (product of Nikken Chemical Co., Ltd., which passes through a 42-mesh screen (350 μm)), and lactose were added to an agitated granulator in amounts shown in Table 1 (formulation indicated under "1"). The ingredients were mixed for 3 minutes and then water (40 ml) was added for granulation. After granulation, the resultant granules were dried by use of a fluidized-bed granulator drier, and sieved through a 16-mesh screen (1000 μm). To the through-sieved granules was added magnesium stearate (0.5% by weight), followed by mixing. The resultant mixture was formed into tablets which are flat-faced and curved eged tablets of 10 mmφ by use of a single-punch tablet machine. Tablets each weighing 400 mg were produced by the application of three different punching pressures. Results of the tests performed on the thus-prepared tablets are shown in Table 2 (columns indicated under "1").

Reference Example 2

For referential purposes, the procedure of Reference Example 1 was repeated based on the formulation shown in Table 1 (formulation indicated under "2") using anhydrous glucose instead of lactose. Results of the tests performed on the thus-prepared tablets are shown in Table 2 (column 2).

Reference Example 3

For referential purposes, the procedure of Reference Example 1 was repeated based on the formulation shown in Table 1 (formulation indicated under "3") using sucrose instead of lactose. Results of the tests performed on the thus-prepared tablets are shown in Table 3 (column 3).

Reference Example 4

For referential purposes, erythritol (product of Nikken Chemical Co., Ltd., which passes through a 42-mesh screen (350 μm)) and lactose, were added to a fluidized-bed granulator drier in amounts shown in Table 1 (formulation indicated under "4"). The ingredients were mixed for 3 minutes and then 5 w/v % polyvinyl alcohol aqueous solution (200 ml) was added for granulation under a spray air pressure of 2 kg/cm$^2$ and at a spray rate of 20 ml/min. After drying, the resultant granules were sieved through a 16-mesh screen (1000 μm). To the through-sieved granules was added magnesium stearate (0.5% by weight), followed by mixing. The resultant mixture was formed into tablets which shape flat-faced and curved eged tablets of 10 mmφ by use of a single-punch tablet machine. Tablets each weighing 400 mg were produced by the application of three different punching pressures. Results of the tests performed on the thus-prepared tablets are shown in Table 3 (columns indicated under "4").

TABLE 1

Formulation

| Component | Reference Examples | | | |
|---|---|---|---|---|
| | 1 | 2 | 3 | 4 |
| Erythritol | 350 g | 350 g | 350 g | 560 g |
| Lactose | 150 g | — | — | 230 g |
| Anhydrous glucose | — | 150 g | — | — |
| Sucrose | — | — | 150 g | — |
| Polyvinyl alcohol | — | — | — | 10 g |
| Total | 500 g | 500 g | 500 g | 800 g |

TABLE 2

Formulation characteristics

| Reference Examples | 1 | | | 2 | | |
|---|---|---|---|---|---|---|
| Punching pressure (kg/stroke) | 598 | 722 | 1063 | 452 | 636 | 1126 |
| (kg/cm$^2$) | 762 | 920 | 1354 | 576 | 810 | 1434 |
| Hardness (kg) | 1.4 | 1.8 | 2.1 | 0.9 | 1.3 | 2.5 |
| Intraoral disintegration or dissolution time (sec) | 37 | 43 | 45 | 46 | 58 | 77 |
| Disintegration time (sec) | 46 | 39 | 30 | 43 | 50 | 65 |
| Fall impact strength (%) | 30 | 10 | 30 | 10 | 30 | 30 |
| Density (mg/cm$^3$) | 1193 | 1210 | 1240 | 1156 | 1207 | 1251 |
| Remarks | Hardness was not improved. Capping occurred at ≧1000 kg/cm$^2$ | | | Hardness was not improved. Capping occurred at ≧1000 kg/cm$^2$ | | |

TABLE 3

Formulation characteristics

| Reference Examples | 3 | | | 4 | | |
|---|---|---|---|---|---|---|
| Punching pressure (kg/stroke) | 467 | 690 | 995 | 695 | 1033 | 1247 |
| (kg/cm$^2$) | 595 | 879 | 1268 | 885 | 1316 | 1588 |
| Hardness (kg) | 1.3 | 2.0 | 2.7 | 2.0 | 3.9 | 4.9 |
| Intraoral disintegration or dissolution time (sec) | 95 | 124 | 150 | 174 | 239 | 261 |
| Disintegration time (sec) | 12 | 12 | 14 | 93 | 112 | 146 |
| Fall impact strength (%) | 10 | 20 | 30 | 10 | 0 | 0 |
| Density (mg/cm$^3$) | 1174 | 1214 | 1243 | 1205 | 1241 | 1252 |
| Remarks | Hardness was not improved. Capping occurred at ≧1000 kg/cm$^2$ | | | Long intraoral disintegration time, No capping | | |

Example 1

Erythritol (product of Nikken Chemical Co., Ltd., which passes through a 42-mesh screen (350 μm)) and corn starch, were added to a fluidized-bed granulator in amounts shown in Table 4 (formulation indicated under "1"). The ingredients were mixed for 3 minutes and then water (800 ml) was added for granulation under a spray air pressure of 2 kg/cm² and at a spray rate of 20 ml/min. After drying, the resultant granules were sieved through a 16-mesh screen (1000 μm). To the through-sieved granules was added magnesium stearate (0.5% by weight), followed by mixing. The resultant mixture was formed into tablets which shape flat-faced and curve eged tablets of 10 mmφ by use of a single-punch tablet. Tablets each weighing 400 mg were produced by the application of three different punching pressures. Results of the tests performed on the thus-prepared tablets are shown in Table 5 (columns indicated under "1").

Example 2

The procedure of Example 1 was repeated based on the formulation shown in Table 4 (formulation indicated under "2") using microcrystalline cellulose instead of corn starch. Results of the tests performed on the thus-prepared tablets are shown in Table 5 (column 2).

Example 3

The procedure of Example 1 was repeated based on the formulation shown in Table 4 (formulation indicated under "3") using corn starch and partly pregelatinized starch instead of corn starch. Results of the tests performed on the thus-prepared tablets are shown in Table 6 (column 3).

Example 4

The procedure of Example 1 was repeated based on the formulation shown in Table 4 (formulation indicated under "4") using corn starch, microcrystalline cellulose, and partly pregelatinized starch instead of corn starch. Results of the tests performed on the thus-prepared tablets are shown in Table 6 (column 4).

TABLE 4

Formulation

| Component | Examples | | | |
|---|---|---|---|---|
| | 1 | 2 | 3 | 4 |
| Erythritol | 560 g | 560 g | 560 g | 560 g |
| Corn starch | 240 g | — | 120 g | 120 g |
| Microcrystallized cellulose | — | 240 g | — | 40 g |
| Partly pregelatinized starch | — | — | 120 g | 80 g |
| Total | 800 g | 800 g | 800 g | 800 g |

TABLE 5

Formulation characteristics

| Example | 1 | | | 2 | | |
|---|---|---|---|---|---|---|
| Punching (kg/stroke) pressure (kg/cm²) | 722 920 | 1091 1390 | 1275 1624 | 531 676 | 696 887 | 1021 1301 |
| Hardness (kg) | 1.9 | 4.0 | 4.9 | 3.6 | 5.0 | 7.3 |
| Intraoral disintegration or dissolution time (sec) | 12 | 16 | 22 | 12 | 17 | 22 |
| Disintegration time (sec) | 15 | 20 | 24 | 10 | 11 | 14 |
| Fall impact strength (%) | 0 | 0 | 0 | 0 | 0 | 0 |
| Density (mg/cm³) | 1162 | 1227 | 1246 | 1121 | 1164 | 1222 |
| Remarks | No capping, No rough sensation | | | No capping, No rough sensation | | |

TABLE 6

Formulation characteristics

| Example | 3 | | | 4 | | |
|---|---|---|---|---|---|---|
| Punching (kg/stroke) pressure (kg/cm²) | 706 899 | 1063 1354 | 1176 1498 | 729 929 | 1016 1294 | 1224 1559 |
| Hardness (kg) | 1.9 | 3.9 | 4.6 | 1.2 | 2.1 | 3.0 |
| Intraoral disintegration or dissolution time (sec) | 13 | 16 | 16 | 18 | 24 | 28 |
| Disintegration time (sec) | 31 | 34 | 35 | 35 | 43 | 37 |
| Fall impact strength (%) | 20 | 0 | 0 | 0 | 0 | 0 |
| Density (mg/cm³) | 1137 | 1195 | 1211 | 1115 | 1164 | 1190 |
| Remarks | No capping, No rough sensation | | | No capping, No rough sensation | | |

Example 5

Erythritol (product of Nikken Chemical Co., Ltd., which passes through a 42-mesh screen (350 μm)) and corn starch, were added to a fluidized-bed granulator in amounts shown in Table 7 (formulation indicated under "5"). The ingredients were mixed for 3 minutes and then 20 w/v % D-mannitol aqueous solution (175 ml) was added for granulation under a spray air pressure of 2 kg/cm² and at a spray rate of 18 ml/min. After drying, the resultant granules were sieved through a 16-mesh screen (1000 μm). To the through-sieved granules was added magnesium stearate (0.5% by weight), followed by mixing. The resultant mixture was formed into tablets by use of a single-punch tablet machine which shape flat-faced and curved eged tablets of 10 mmφ. Tablets each weighing 400 mg were produced by the application of three different punching pressures. Results of the tests performed on the thus-prepared tablets are shown in Table 8 (columns indicated under "5").

Example 6

The procedure of Example 5 was repeated based on the formulation shown in Table 7 (formulation indicated under "6") using corn starch and microcrystalline cellulose instead of corn starch. Results of the tests performed on the thus-prepared tablets are shown in Table 8 (column 6).

TABLE 7

Formulation

| Component | Examples | |
|---|---|---|
| | 5 | 6 |
| Erythritol | 560 g | 560 g |
| Corn starch | 205 g | 45 g |
| Microcrystalline cellulose | — | 160 g |
| D-Mannitol | 35 g | 35 g |
| Total | 800 g | 800 g |

TABLE 8

Formulation characteristics

| Examples | 5 | | | 6 | | |
|---|---|---|---|---|---|---|
| Punching (kg/stroke) pressure (kg/cm²) | 826 1052 | 1037 1321 | 1446 1842 | 552 703 | 703 895 | 920 1172 |
| Hardness (kg) | 0.9 | 1.5 | 3.0 | 3.1 | 4.3 | 5.9 |

TABLE 8-continued

Formulation characteristics

| Examples | 5 | | | 6 | | |
|---|---|---|---|---|---|---|
| Intraoral disintegration or dissolution time (sec) | 19 | 23 | 29 | 23 | 27 | 33 |
| Disintegration time (sec) | 24 | 27 | 28 | 26 | 26 | 26 |
| Fall impact strength (%) | 20 | 10 | 0 | 0 | 0 | 0 |
| Density (mg/cm$^3$) | 1135 | 1169 | 1218 | 1128 | 1168 | 1205 |
| Remarks | No capping, No rough sensation | | | No capping, No rough sensation | | |

Example 7

Erythritol (product of Nikken Chemical Co., Ltd., which passes through a 42-mesh screen (350 μm)) and corn starch, were added to a fluidized-bed granulator in amounts shown in Table 9 (formulation indicated under "7"). The ingredients were mixed for 3 minutes and then 70 w/v % aqueous xylitol solution (32 ml) was added for granulation under a spray air pressure of 2 kg/cm$^2$ and at a spray rate of 6 ml/min. After drying, the resultant granules were sieved through a 16-mesh screen (1000 μm). To the through-sieved granules was added magnesium stearate (0.5% by weight), followed by mixing. The resultant mixture was formed into tablets which are flat-faced and curved eged tablets of 10 mmφ use of a single-punch tablet machine. Tablets each weighing 400 mg were produced by the application of three different punching pressures. Results of the tests performed on the thus-prepared tablets are shown in Table 10 (columns indicated under "7").

Example 8

The procedure of Example 7 was repeated based on the formulation shown in Table 9 (formulation indicated under "8") adding corn starch and microcrystalline cellulose instead of corn starch and mixing for 3 minutes, and then using 8 w/v % aqueous xylitol solution (200 ml). Results of the tests performed on the thus-prepared tablets are shown in Table 10 (column 8).

TABLE 9

Formulation

| | Examples | |
|---|---|---|
| Component | 7 | 8 |
| Erythritol | 560 g | 560 g |
| Corn starch | 217.6 g | 64 g |
| Microcrystalline cellulose | — | 160 g |
| Xylitol | 22.4 g | 16 g |
| Total | 800 g | 800 g |

TABLE 10

Formulation characteristics

| Examples | 7 | | | 8 | | |
|---|---|---|---|---|---|---|
| Punching (kg/stroke) | 836 | 1009 | 1259 | 481 | 713 | 837 |
| pressure (kg/cm$^2$) | 1065 | 1285 | 1604 | 613 | 908 | 1066 |
| Hardness (kg) | 1.1 | 1.4 | 2.2 | 2.9 | 5.3 | 6.3 |

TABLE 10-continued

Formulation characteristics

| Examples | 7 | | | 8 | | |
|---|---|---|---|---|---|---|
| Intraoral disintegration or dissolution time (sec) | 20 | 22 | 26 | 15 | 23 | 31 |
| Disintegration time (sec) | 63 | 57 | 65 | 23 | 25 | 30 |
| Fall impact strength (%) | 10 | 10 | 0 | 0 | 0 | 0 |
| Density (mg/cm$^3$) | 1139 | 1165 | 1191 | 1109 | 1171 | 1195 |
| Remarks | No Capping, No rough sensation | | | No Capping, No rough sensation | | |

Example 9

Erythritol (product of Nikken Chemical Co., Ltd., which passes through a 42-mesh screen (350 μm)) and synthetic hydrotalcite, were added to a fluidized-bed granulator in amounts shown in Table 11 (formulation indicated under "9"). The ingredients were mixed for 3 minutes and then water (800 ml) was added for granulation under a spray air pressure of 2 kg/cm$^2$ and at a spray rate of 20 ml/min. After drying, the resultant granules were sieved through a 16-mesh screen (1000 μm). To the through-sieved granules was added magnesium stearate (0.5% by weight), followed by mixing. The resultant mixture was formed into tablets which are flat-faced and curved eged tablets of 10 mmφ by use of a single-punch tablet machine. Tablets each weighing 400 mg were produced by the application of three different punching pressures. Results of the tests performed on the thus-prepared tablets are shown in Table 12 (columns indicated under "9").

Example 10

The procedure of Example 9 was repeated based on the formulation shown in Table 11 (formulation indicated under "10") using precipitated calcium carbonate instead of synthetic hydrotalcite. Results of the tests performed on the thus-prepared tablets are shown in Table 12 (column 10).

TABLE 11

Formulation

| | Examples | |
|---|---|---|
| Component | 9 | 10 |
| Erythritol | 560 g | 560 g |
| Synthetic hydrotalcite | 240 g | — |
| Precipitated calcium carbonate | — | 240 g |
| Total | 800 g | 800 g |

TABLE 12

Formulation charaateristics

| Examples | 9 | | | 10 | | |
|---|---|---|---|---|---|---|
| Punching (kg/stroke) | 696 | 833 | 1245 | 760 | 945 | |
| pressure (kg/cm$^2$) | 887 | 1062 | 1586 | 968 | 1204 | |
| Hardness (kg) | 2.1 | 2.8 | 5.5 | 2.1 | 2.7 | |
| Intraoral disintegration or dissolution time (sec) | 13 | 14 | 19 | 42 | 47 | |

TABLE 12-continued

Formulation charaateristics

| Examples | 9 | | | 10 | |
|---|---|---|---|---|---|
| Disintegration time (sec) | 19 | 21 | 21 | 106 | 100 |
| Fall impact strength (%) | 0 | 0 | 0 | 20 | 10 |
| Density (mg/cm$^3$) | 1106 | 1132 | 1197 | 1301 | 1326 |
| Remarks | | No capping, No rough sensation | | | No capping, no rough sensation |

Example 11

Erythritol (product of Nikken Chemical Co., Ltd., which passes through a 42-mesh screen (350 μm)) and ascorbic acid, were added to a fluidized-bed granulator in amounts shown in Table 13 (formulation indicated under "11"). The ingredients were mixed for 3 minutes and then water (240 ml) was added for granulation under a spray air pressure of 1.5 kg/cm$^2$ and at a spray rate of 24 ml/min. After drying, the resultant granules were sieved through a 16-mesh screen (1000 μm). To the through-sieved granules were added microcrystalline cellulose in amounts shown in Table 13 (formulation indicated under "11") and magnesium stearate (0.5% by weight), followed by mixing. The resultant mixture was formed into tablets which are flat-faced and curved eged tablets of 10 mmϕ by use of a single-punch tablet machine. Tablets each weighing 400 mg were produced by the application of three different punching pressures. Results of the tests performed on the thus-prepared tablets are shown in Table 14 (columns indicated under "11").

Example 12

The procedure of Example 11 was repeated based on the formulation shown in Table 13 (formulation indicated under "12") using thiamine nitrate instead of ascorbic acid. Results of the tests performed on the thus-prepared tablets are shown in Table 14 (column 12).

TABLE 13

Formulation

| | Examples | |
|---|---|---|
| Component | 11 | 12 |
| Erythritol | 240 g | 380 g |
| Ascorbic acid | 40 g | — |
| Thiamine nitrate | — | 20 g |
| Crystalline cellulose | 120 g | 40 g |
| Total | 400 g | 440 g |

TABLE 14

Formulation characteristics

| Examples | 11 | | | 12 | | |
|---|---|---|---|---|---|---|
| Punching pressure (kg/stroke) | 361 | 546 | 1039 | 275 | 1125 | 1425 |
| (kg/cm$^2$) | 460 | 696 | 1324 | 350 | 1433 | 1815 |
| Hardness (kg) | 3.5 | 5.3 | 9.8 | 0.5 | 2.1 | 3.0 |
| Intraoral disintegration or dissolution time (sec) | 25 | 31 | 43 | 16 | 22 | 20 |

TABLE 14-continued

Formulation characteristics

| Examples | 11 | | | 12 | | |
|---|---|---|---|---|---|---|
| Disintegration time (sec) | 10 | 17 | 42 | 16 | 17 | 20 |
| Fall impact strength (%) | 0 | 0 | 0 | 10 | 0 | 0 |
| Density (mg/cm$^3$) | 1110 | 1221 | 1317 | 1113 | 1254 | 1286 |
| Remarks | | No capping, No rough sensation | | | No capping, No rough sensation | |

Example 13

Erythritol (product of Nikken Chemical Co., Ltd., which passes through a 42-mesh screen (350 μm)), cimetidine, microcrystalline cellulose, and low substituted hydroxypropylcellulose, respectively in amounts shown in Table 15, were added to a fluidized-bed granulator. The ingredients were mixed for 3 minutes and then 8 w/v % D-mannitol aqueous solution (100 ml) was added for granulation under a spray air pressure of 1.5 kg/cm$^2$ and at a spray rate of 20 ml/min. After drying, the resultant granules were sieved through a 16-mesh screen (1000 μm). To the through-sieved granules were added magnesium stearate (0.5% by weight), followed by mixing. The resultant mixture was formed into tablets which are flat-faced and curved eged tablets of 10 mmϕ by use of a single punch tablet machine. Tablets each weighing 400 mg were produced by the application of three different punching pressures. Results of the tests performed on the thus-prepared tablets are shown in Table 16.

TABLE 15

Formulation

| Component | Examples 13 |
|---|---|
| Erythritol | 342 g |
| Cimetidine | 50 g |
| Microcrystalline cellulose | 20 g |
| Low-substituted hydroxypropylcellulose | 20 g |
| D-Mannitol | 8 g |
| Total | 440 g |

TABLE 16

Formulation characteristics

| | Examples 13 | | |
|---|---|---|---|
| Punching pressure | | | |
| (kg/stroke) | 275 | 595 | 1450 |
| (kg/cm$^2$) | 350 | 758 | 1847 |
| Hardness (kg) | 0.6 | 1.3 | 4.1 |
| Intraoral disintegration or dissolution time (sec) | 31 | 30 | 38 |
| Disintegration time (sec) | 22 | 22 | 25 |
| Fall impact strength (%) | 20 | 0 | 0 |
| Density (mg/cm$^3$) | 1101 | 1205 | 1322 |
| Remarks | | No capping, No rough sensation | |

Example 14

(1) Cetraxate hydrochloride (5400 g), aspartame (81 g), and corn starch (275.4 g) were added to a fluidized-bed granlator. The ingredients were mixed for 3 minutes and then 3 w/v % polyvinyl alcohol solution (2520 ml) containing scopolia extract (108 g) was added for granulation under a spray air pressure of 1.75 kg/cm$^2$ and at a spray rate of 120 ml/min. After drying, the resultant granules were sieved for regulation through a 16-mesh screen (1000 μm) to obtain granules A.

(2) Precipitated calcium carbonate (3000 g), magnesium hydroxide (1500 g), erythritol (1050 g), and corn starch (240 g) were added to a fluidized-bed granulator. The ingredients were mixed for 3 minutes and then 3 w/v % polyvinyl alcohol solution (2000 ml) was added for granulation under a spray air pressure of 2.75 kg/cm$^2$ and at a spray rate of 120 ml/min. After drying, the resultant granules were sieved through a 16-mesh screen (1000 μm) to obtain granules B.

(3) Erythritol (5490 g) and cornstarch (306 g) were added to a fluidized-bed granulator. Then 10 w/v % scopolia extract solution (540 ml) and purified water (1700 ml) were added for granulation under a spray air pressure of 1.5 kg/cm$^2$ and at a spray rate of 120 ml/min. After drying, the resultant granules were sieved through a 16-mesh screen (1000 μm) to obtain granules C.

(4) Light anhydrous silicic acid (6 g) and corn starch (102 g) were added to 1-menthol (12 g). The ingredients were mixed well and in a mortar to obtain ten-fold-diluted powder in 1-menthol.

(5) Granules A (660 g) obtained from the above (1), granules B (1170 g) obtained from the above (2), and granules C (1950 g) obtained from the above (3) were weighed respectively. To the ingredients were added 60 g of the ten-fold-diluted powder in 1-menthol obtained from the above (4) and 45 g of magnesium stearate, followed mixing. The resultant mixture was formed into tablets by use of a single-punch tablet machine which is equiped with a standard concave punch having a diameter of 13 mmφ. Tablets each weighing 647.5 mg were produced by the application of three different punching pressures. Results of the tests performed on the thus-prepared tablets are shown in Table 18.

TABLE 17

Formulation characteristics

| Component | Feed (g) |
| --- | --- |
| Granule A | |
| Cetraxate hydrochloride | 5400 |
| Scopolia extract | 108 |
| Aspartame | 81 |
| Polyvinyl alcohol | 75.6 |
| Corn starch | 275.4 |
| Subtotal | 5940 |
| Granule B | |
| Precipitated calcium carbonate | 3000 |
| Magnesium hydroxide | 1500 |
| Polyvinyl alcohol | 60 |
| Erythritol | 1050 |
| Corn starch | 240 |
| Subtotal | 5850 |

TABLE 17-continued

Formulation characteristics

| Component | Feed (g) |
| --- | --- |
| Granule C | |
| Scopolia extract | 54 |
| Erythritol | 5490 |
| Corn starch | 306 |
| Subtotal | 5850 |

TABLE 18

Formulation characteristics

| Punching pressure (kg) | Punching pressure (kg/cm$^2$) | Hardness (kg) | Disintegration time in the oral cavity (sec) | Disintegration time (sec) |
| --- | --- | --- | --- | --- |
| 841 | 634 | 4.3 | 64.9 | 32.8 |
| 1031 | 777 | 4.8 | 75.1 | 29.9 |
| 1328 | 1001 | 6.3 | 85.6 | 31.4 |

Example 15

Erythritol (product of Nikken Chemical Co., Ltd., which passes through a 42-mesh screen (350 μm)), corn starch, anhydrous caffeine, thiamine nitrate, pyridoxin hydrochloride, calcium pantothenate, nicotinamide, and aspartame in amounts shown in Table 19 were added to a fluidized-bed granulator. The ingredients were mixed for 3 minutes and then 5 w/v % aqueous coffee-extract solution (100 ml) was added for granulation under a spray air pressure of 1.5 kg/cm$^2$ and at a spray rate of 15 ml/min. After drying, the resultant granules were sieved through a 16-mesh screen (1000 μm). To the through-sieved granules were added the ten-fold-diluted powder in 1-menthol (1% by weight) (To 8.5 parts by weight of corn starch were added 1 part by weight of 1-menthol and 0.5 parts by weight of light anhydrous silicic acid. The powder was obtained by mixing the ingredients and crushing them in a mortar.) and magnesium stearate (0.5% by weight), followed by mixing. The resultant mixture was formed into tablets which are flat-faced and curved eged tablets of 8 mmφ by use of a single-punch tablet machine. Tablets each weighing 240 mg were produced by the application of two different punching pressures. Results of the tests performed on the thus-prepared tablets are shown in Table 20.

TABLE 19

| Component | Example 15 |
| --- | --- |
| Erythritol | 176 g |
| Corn starch | 334 g |
| Anhydrous caffeine | 50 g |
| Thiamine nitrate | 3.3 g |
| Pyridoxin hydrochloride | 1.7 g |
| Calcium pantothenate | 7 g |
| Nicotinamide | 5 g |
| Coffee extract | 5 g |
| Aspartame | 18 g |
| Total | 600 g |

TABLE 20

| | Formulation characteristics | |
|---|---|---|
| | Example | |
| | 15 | |
| Punching pressure | | |
| (kg/stroke) | 618 | 1025 |
| (kg/cm²) | 1230 | 2040 |
| Hardness (kg) | 0.5 | 2.0 |
| Intraoral disintegration or dissolution time (sec) | 30 | 45 |
| Disintegration time (sec) | 40 | 67 |
| Fall impact strength (%) | 40 | 0 |
| Density (mg/cm³) | 960 | 960 |

Industrial Applicability

The rapidly disintegratable compression-molded material of the present invention disintegrates and dissolves rapidly when placed in the oral cavity or in water. Therefore, it can be taken easily. It also has enhanced hardness, exhibiting excellent storage stability in the process of manufacture and distribution.

Accordingly, in accordance with the pharmaceutical agents contained therein, it can be advantageously used for the treatment and prevention of diseases suffered by patients, particularly elderly citizens, children, and patients who have difficulty in swallowing.

Moreover, according to the process for the manufacture of the present invention, the rapidly disintegratable compression-molded material exhibiting excellent characteristics as described above can be produced very easily without requiring intricate manufacture steps or special facility.

Furthermore, since the process of the present invention uses a dry tableting method, the material can be formed into tablets of multi-type granules or into multi-layer tablets. In addition, the present process is applicable for the manufacture of drug formulations in which a plurality of ingredients are contained in mutually varying amounts.

What is claimed is:

1. A quickly disintegratable compression-molded material, comprising:
   an excipient (a); and
   erythritol (b);
   wherein said compression-molded material has a density of 800–1600 mg/cm³.

2. The quickly disintegratable compression-molded material according to claim 1, wherein a total amount of said excipient (a) and said erythritol (b) falls within the range of 30–99% by weight of a total weight of said compression-molded material.

3. The quickly disintegratable compression-molded material according to claim 2, wherein the total amount of said excipient (a) and said erythritol (b) falls within the range of 50–99% by weight of the total weight of said compression-molded material.

4. The quickly disintegratable compression-molded material according to claim 2, wherein the total amount of said excipient (a) and said erythritol (b) falls within the range of 70–99% by weight of the total weight of said compression-molded material.

5. The quickly disintegratable compression-molded material according to claim 1, wherein a ratio of said excipient (a) and said erythritol (b) is 5–99% by weight of a total weight of said compression-molded material.

6. The quickly disintegratable compression-molded material according to claims 5, wherein the ratio of said excipient (a) and said erythritol (b) is 10–70% by weight of the total weight of said composition.

7. The quickly disintegratable compression-molded material according to claim 5, wherein the ratio of said excipient (a) and said erythritol (b) is 20–50% by weight of the total weight of said compression-molded material.

8. The quickly disintegratable compression-molded material according to claim 1, wherein said excipient is selected from the group consisting of starch, cellulose, sugar alcohol, synthetic hydrotalcite, precipitated calcium carbonate, anhydrous dibasic calcium phosphate, and mixtures thereof.

9. The quickly disintegratable compression-molded material according to claim 8, wherein said starch is selected from the group consisting of corn starch, potato starch, partly pre-gelatinized starch, pre-gelatinized starch, and mixtures thereof.

10. The quickly disintegratable compression-molded material according to claim 8, wherein said cellulose is selected from the group consisting of microcrystalline cellulose, powdered cellulose, low substituted hydroxypropylcellulose, carmellose, and mixtures thereof.

11. The quickly disintegratable compression-molded material according to claim 8, wherein said sugar alcohol is selected from the group consisting of D-mannitol, xylitol, maltitol, and mixtures thereof.

12. The quickly disintegratable compression-molded material according to claim 1, wherein said material further comprises an active ingredient (c).

13. The quickly disintegratable compression-molded material according to claim 12, wherein said active ingredient (c) is selected from the group consisting of vitamins, antipyretic analgesic antiinflammatory agents, antihistaminic agents, antitussives, bactericides, antacids, crude drugs, gastoric mucosal protective agents, $H_2$ receptor antagonists, analgetic antispasmodic agents, anticonstipation agents, antibiotics, antihypertensives, antiarrhythmic agents, gastrointestinal agents, expectorant drugs, antivertigos, and central nervous system stimulants.

14. The quickly disintegratable compression-molded material according to claim 12, wherein said active ingredient (c) is an antiulcer drug.

15. The quickly disintegratable compression-molded material according to claim 12, wherein said active ingredient (c) is selected from the group consisting of cetraxate hydrochloride, cimetidine, famotidine, ranitidine hydrochloride, nizatidine, and roxatidine acetate hydrochloride.

16. The quickly disintegratable compression-molded material according to claim 1, wherein said compression-molded material is a tablet.

17. The quickly disintegratable compression-molded material according to claim 1, wherein said compression-molded material when measured according to the disintegration test method of Japanese Pharmacopoeia $12^{th}$ Revision, disintegrates or dissolves within 60 seconds for the case in which the diameter or the major length of the compression-molded material is less than 8 mm; within 90 seconds for the case of the size being not less than 8 mm and less than 10 mm; within 120 seconds for the case of the size being not less than between 10 mm and less than 15 mm; within 180 seconds for the case of the size being not less than between 15 mm and less than 20 mm; and within 240 seconds for the case of the size being not less than 20 mm.

18. The quickly disintegratable compression-molded material according to claim 1, wherein said compression-molded material when placed in the oral cavity, disintegrates or dissolves within 40 seconds for the case in which the diameter or the major length of the compression-molded material is less than 8 mm; within 60 seconds for the case of the size being not less than 8 mm and less than 10 mm; within 90 seconds for the case of the size being not less than between 10 mm and less than 15 mm; within 120 seconds for the case of the size being not less than between 15 mm and less than 20 mm; and within 180 seconds for the case of the size being not less than 20 mm.

19. The quickly disintegratable compression-molded material according to claim 1, wherein said compression-molded material has a hardness of 0.5 kg or more for the case in which the diameter or the major length of the compression-molded material is less than 8 mm; a hardness of 1 kg or more for the case in which the diameter or the major length of the compression-molded material is not less than 8 mm and less than 10 mm; a hardness of 2 kg or more for the case in which the diameter or the major length of the compression-molded material is not less than 10 mm and less than 15 mm; a hardness of 3 kg or more for the case in which the diameter or the major length of the compression-molded material is not less than 15 mm and less than 20 mm; a hardness of 4 kg or more for the case in which the diameter or the major length of the compression-molded material is not less than 20 mm.

20. The quickly disintegratable compression-molded material according to claim 1, wherein said composition is substantially dry.

21. A compression-molded material prepared by a process, comprising:
compression-molding a composition comprising an excipient (a) and erythritol (b), without adding water;
wherein said compression-molded material has a density of 800–1600 mg/cm$^3$.

22. The compression-molded material according to claim 21, wherein a total amount of said excipient (a) and said erythritol (b) falls within the range of 30–99% by weight of a total weight of said compression-molded material.

23. The compression-molded material according to claim 22, wherein the total amount of said excipient (a) and said erythritol (b) falls within the range of 50–99% by weight of the total weight of said compression-molded material.

24. The compression-molded material according to claim 22, wherein the total amount of said excipient (a) and said erythritol (b) falls within the range of 70–99% by weight of the total weight of said compression-molded material.

25. The compression-molded material according to claim 21, wherein a ratio of said excipient (a) and said erythritol (b) is 5–99% by weight of a total weight of said compression-molded material.

26. The compression-molded material according to claim 25, wherein the ratio of said excipient (a) and said erythritol (b) is 10–70% by weight of the total weight of said composition.

27. The compression-molded material according to claim 25, wherein the ratio of said excipient (a) and said erythritol (b) is 20–50% by weight of the total weight of said compression-molded material.

28. The compression-molded material according to claim 21, wherein said excipient is selected from the group consisting of starch, cellulose, sugar alcohol, synthetic hydrotalcite, precipitated calcium carbonate, anhydrous dibasic calcium phosphate, and mixtures thereof.

29. The compression-molded material according to claim 28, wherein said starch is selected from the group consisting of corn starch, potato starch, partly pre-gelatinized starch, pre-gelatinized starch, and mixtures thereof.

30. The compression-molded material according to claim 28, wherein said cellulose is selected from the group consisting of microcrystalline cellulose, powdered cellulose, low substituted hydroxypropylcellulose, carmellose, and mixtures thereof.

31. The compression-molded material according to claim 28, wherein said sugar alcohol is selected from the group consisting of D-mannitol, xylitol, maltitol, and mixtures thereof.

32. The compression-molded material according to claim 21, wherein said composition further comprises an active ingredient (c).

33. The compression-molded material according to claim 32, wherein said active ingredient (c) is selected from the group consisting of vitamins, antipyretic analgesic antiinflammatory agents, antihistaminic agents, antitussives, bactericides, antacids, crude drugs, gastoric mucosal protective agents, H$_2$ receptor antagonists, analgetic antispasmodic agents, anticonstipation agents, antibiotics, antihypertensives, antiarrhythmic agents, gastrointestinal agents, expectorant drugs, antivertigos, and central nervous system stimulants.

34. The compression-molded material according to claim 32, wherein said active ingredient (c) is an antiulcer drug.

35. The compression-molded material according to claim 32, wherein said active ingredient (c) is selected from the group consisting of cetraxate hydrochloride, cimetidine, famotidine, ranitidine hydrochloride, nizatidine, and roxatidine acetate hydrochloride.

36. The compression-molded material according to claim 21, wherein said compression-molded material is a tablet.

37. The quickly disintegratable compression-molded material according to claim 1, wherein said compression-molded material is prepared without drying.

38. The compression-molded material according to claim 21, wherein said compression-molded material when measured according to the disintegration test method of Japanese Pharmacopoeia 12$^{th}$ Revision, disintegrates or dissolves within 60 seconds for the case in which the diameter or the major length of the compression-molded material is less than 8 mm; within 90 seconds for the case of the size being not less than 8 mm and less than 10 mm; within 120 seconds for the case of the size being not less than between 10 mm and less than 15 mm; within 180 seconds for the case of the size being not less than between 15 mm and less than 20 mm; and within 240 seconds for the case of the size being not less than 20 mm.

39. The compression-molded material according to claim 21, wherein said compression-molded material when placed in the oral cavity, disintegrates or dissolves within 40 seconds for the case in which the diameter or the major length of the compression-molded material is less than 8 mm; within 60 seconds for the case of the size being not less than 8 mm and less than 10 mm; within 90 seconds for the case of the size being not less than between 10 mm and less than 15 mm; within 120 seconds for the case of the size being not less than between 15 mm and less than 20 mm; and within 180 seconds for the case of the size being not less than 20 mm.

40. The compression-molded material according to claim 21, wherein said compression-molded material has a hardness of 0.5 kg or more for the case in which the diameter or the major length of the compression-molded material is less than 8 mm; a hardness of 1 kg or more for the case in which the diameter or the major length of the compression-molded material is not less than 8 mm and less than 10 mm; a hardness of 2 kg or more for the case in which the diameter or the major length of the compression-molded material is not less than 10 mm and less than 15 mm; a hardness of 3 kg or more for the case in which the diameter or the major length of the compression-molded material is not less than 15 mm and less than 20 mm; a hardness of 4 kg or more for the case in which the diameter or the major length of the compression-molded material is not less than 20 mm.

41. The compression-molded material according to claim 21, wherein said composition is substantially dry.

42. The compression-molded material according to claim 21, wherein said compression-molded material is prepared without drying.

43. A process, comprising:
compression-molding a composition comprising (a) an excipient and (b) erythritol without adding water;
wherein a pressure of said compression-molding is 400–2000 kg/cm$^2$.

44. The process according to claim 43, wherein said compression-molding is tableting.

45. The process according to claim 43, without drying.

46. The process according to claim 43, wherein said excipient is selected from the group consisting of starch, cellulose, sugar alcohol, synthetic hydrotalcite, precipitated calcium carbonate, anhydrous dibasic calcium phosphate, and mixtures thereof.

47. The process according to claim 46, wherein said starch is selected from the group consisting of corn starch, potato starch, partly pre-gelatinized starch, pre-gelatinized starch, and mixtures thereof.

48. The process according to claim 46, wherein said cellulose is selected from the group consisting of microcrystalline cellulose, powdered cellulose, low substituted hydroxypropylcellulose, carmellose, and mixtures thereof.

49. The process according to claim 46, wherein said sugar alcohol is selected from the group consisting of D-mannitol, xylitol, maltitol, and mixtures thereof.

50. The process according to claim 43, wherein said composition further comprises an active ingredient (c).

51. The process according to claim 50, wherein said active ingredient (c) is selected from the group consisting of vitamins, antipyretic analgesic antiinflammatory agents, antihistaminic agents, antitussives, bactericides, antacids, crude drugs, gastoric mucosal protective agents, $H_2$ receptor antagonists, analgetic antispasmodic agents, anticonstipation agents, antibiotics, antihypertensives, antiarrhythmic agents, gastrointestinal agents, expectorant drugs, antivertigos, and central nervous system stimulants.

52. The process according to claim 50, wherein said active ingredient (c) is an antiulcer drug.

53. The process according to claim 50, wherein said active ingredient (c) is selected from the group consisting of cetraxate hydrochloride, cimetidine, famotidine, ranitidine hydrochloride, nizatidine, and roxatidine acetate hydrochloride.

54. The process according to claim 43, wherein a total amount of said excipient (a) and said erythritol (b) falls within the range of 30–99% by weight of a total weight of said compression-molded material.

55. The process according to claim 54, wherein the total amount of said excipient (a) and said erythritol (b) falls within the range of 50–99% by weight of the total weight of said compression-molded material.

56. The process according to claim 54, wherein the total amount of said excipient (a) and said erythritol (b) falls within the range of 70–99% by weight of the total weight of said compression-molded material.

57. The process according to claim 43, wherein a ratio of said excipient (a) and said erythritol (b) is 5–99% by weight of a total weight of said compression-molded material.

58. The process according to claim 57, wherein the ratio of said excipient (a) to said erythritol (b) is 10–70% by weight of the total weight of said compression-molded material.

59. The process according to claim 57, wherein the ratio of said excipient (a) and said erythritol (b) is 20–50% by weight of the total weight of said compression-molded material.

60. The process according to claim 43, wherein said compression-molded material is a tablet.

61. The process according to claim 43, wherein said compression-molded material has a density of 800–1600 mg/cm$^3$.

62. The process according to claim 43, wherein said compression-molded material when measured according to the disintegration test method of Japanese Pharmacopoeia 12$^{th}$ Revision, disintegrates or dissolves within 60 seconds for the case in which the diameter or the major length of the compression-molded material is less than 8 mm; within 90 seconds for the case of the size being not less than 8 mm and less than 10 mm; within 120 seconds for the case of the size being not less than between 10 mm and less than 15 mm; within 180 seconds for the case of the size being not less than between 15 mm and less than 20 mm; and within 240 seconds for the case of the size being not less than 20 mm.

63. The process according to claim 43, wherein said compression-molded material when placed in the oral cavity, disintegrates or dissolves within 40 seconds for the case in which the diameter or the major length of the compression-molded material is less than 8 mm; within 60 seconds for the case of the size being not less than 8 mm and less than 10 mm; within 90 seconds for the case of the size being not less than between 10 mm and less than 15 mm; within 120 seconds for the case of the size being not less than between 15 mm and less than 20 mm; and within 180 seconds for the case of the size being not less than 20 mm.

64. The process according to claim 43, wherein said compression-molded material has a hardness of 0.5 kg or more for the case in which the diameter or the major length of the compression-molded material is less than 8 mm; a hardness of 1 kg or more for the case in which the diameter or the major length of the compression-molded material is not less than 8 nun and less than 10 mm; a hardness of 2 kg or more for the case in which the diameter or the major length of the compression-molded material is not less than 10 mm and less than 15 mm; a hardness of 3 kg or more for the case in which the diameter or the major length of the compression-molded material is not less than 15 mm and less than 20 mm; a hardness of 4 kg or more for the case in which the diameter or the major length of the compression-molded material is not less than 20 mm.

65. The process according to claim 43, wherein said composition is substantially dry.

\* \* \* \* \*